US012642585B2

(12) United States Patent　　　　　(10) Patent No.:　US 12,642,585 B2
Altman et al.　　　　　　　　　　　　(45) Date of Patent:　　　Jun. 2, 2026

(54) DETECTION OF ELECTROPHYSIOLOGICAL (EP) CONDUCTION GAPS IN ABLATION LINE

(71) Applicant: BIOSENSE WEBSTER (ISRAEL) LTD., Yokneam (IL)

(72) Inventors: Sigal Altman, Ramat Hashofet (IL); Meytal Segev, Haifa (IL); Akram Zoabi, Haifa (IL); Fady Massarwa, Baka al Gharbiyya (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 815 days.

(21) Appl. No.: 17/959,394

(22) Filed: Oct. 4, 2022

(65) Prior Publication Data

US 2024/0115312 A1　　　Apr. 11, 2024

(51) Int. Cl.
　　　*A61B 18/14*　　　(2006.01)
　　　*A61B 18/00*　　　(2006.01)
(52) U.S. Cl.
　　　CPC　*A61B 18/1492* (2013.01); *A61B 2018/00357* (2013.01); *A61B 2018/00375* (2013.01); *A61B 2018/00577* (2013.01); *A61B 2018/00672* (2013.01); *A61B 2018/00839* (2013.01)
(58) Field of Classification Search
　　　CPC ...... A61B 18/1492; A61B 2018/00357; A61B 2018/00375; A61B 2018/00577; A61B 2018/00672; A61B 2018/00839; A61B 5/341; A61B 5/367
　　　See application file for complete search history.

(56) References Cited

U.S. PATENT DOCUMENTS

| | | | |
|---|---|---|---|
| 5,391,199 | A | 2/1995 | Ben-Haim |
| 5,443,489 | A | 8/1995 | Ben-Haim |
| 5,558,091 | A | 9/1996 | Acker et al. |
| 6,172,499 | B1 | 1/2001 | Ashe |
| 6,239,724 | B1 | 5/2001 | Doron et al. |
| 6,332,089 | B1 | 12/2001 | Acker et al. |

(Continued)

FOREIGN PATENT DOCUMENTS

| | | |
|---|---|---|
| EP | 3878390 A1 | 9/2021 |
| EP | 3923796 A1 | 12/2021 |
| WO | 2020227469 A1 | 11/2020 |

OTHER PUBLICATIONS

Yavin: "Propagation Vectors Facilitate Differentiation Between Conduction Block, Slow Conduction, and Wavefront Collision", Arrhythmia and Electrophysiology, vol. 14, Aug. 2021 (Aug. 2021), pp. 741-750, (Year: 2021).*

(Continued)

*Primary Examiner* — Tigist S Demie
(74) *Attorney, Agent, or Firm* — Clayton, McKay & Bailey, PC

(57)　　　　　ABSTRACT

A system includes an interface and a processor. The interface is configured to receive multiple electrophysiological (EP) signals from a tissue area along an ablation curve inside a cardiac chamber of a heart of a patient. The processor is configured to (i) generate local conduction vectors (LCVs) for the area based on the multiple EP signals, (ii) estimate a level of change between sets of LCVs along the ablation curve within the tissue area, and (iii) based on the level of change, identify a presence of a conduction gap in the ablation curve.#

14 Claims, 4 Drawing Sheets

(56) References Cited

U.S. PATENT DOCUMENTS

| | | | |
|---|---|---|---|
| 6,484,118 B1 | 11/2002 | Govari | |
| 6,618,612 B1 | 9/2003 | Acker et al. | |
| 6,690,963 B2 | 2/2004 | Ben-Haim et al. | |
| 6,788,967 B2 | 9/2004 | Ben-Haim et al. | |
| 6,892,091 B1 | 5/2005 | Ben-Haim et al. | |
| 7,536,218 B2 | 5/2009 | Govari et al. | |
| 7,756,576 B2 | 7/2010 | Levin | |
| 7,848,787 B2 | 12/2010 | Osadchy | |
| 7,869,865 B2 | 1/2011 | Govari et al. | |
| 8,456,182 B2 | 6/2013 | Bar-Tal et al. | |
| 10,792,087 B2 | 10/2020 | Altmann | |
| 11,083,517 B2 | 8/2021 | Monir | |
| 2013/0006238 A1* | 1/2013 | Ditter | A61B 18/1492 |
| | | | 606/41 |
| 2019/0125438 A1 | 5/2019 | Berman et al. | |
| 2020/0315484 A1 | 10/2020 | Deno | |
| 2023/0093600 A1 | 3/2023 | Govari et al. | |

OTHER PUBLICATIONS

Raphael P. Martins, et al., "Localization of Residual Conduction Gaps After Wide Antral Circumferential Ablation of Pulmonary Veins", JACC: Clinical Electrophysiology, vol. 5, No. 7, Jul. 2019, 753-65.
International Search Report for Corresponding PCT Appln. No. PCT/IB2023/059924dated Jan. 12, 2024.
Yavin: "Propagation Vectors Facilitate 1-10 Differentiation Between Conduction Block, Slow Conduction, and Wavefront Collision", Arrhythmia and Electrophysiology, vol. 14, Aug. 2021 (Aug. 2021), pp. 741-550.
Iden L et al: "First experience and 1-10 validation of the extended early meets late (EEML) tool as part of the novel CARTO software HD Coloring", Journal of Interventional Cardiac Electrophysiology, vol. 60, No. 2, Apr. 6, 2020 (Apr. 6, 2020), pp. 279-285.
Takigawa Masateru et al: "Confirmation of 1-10 the achievement of linear lesions using "activation vectors" based on omnipolar technology", Heart Rhythm, Elsevier, US, vol. 19, No. 11, Aug. 9, 2022 (Aug. 9, 2022), pp. 1792-1801.
S-PO01-175 Ed—Fogel 1-7 Richard, Heart Rhythm, vol. 16, No. 5, 2019.

* cited by examiner

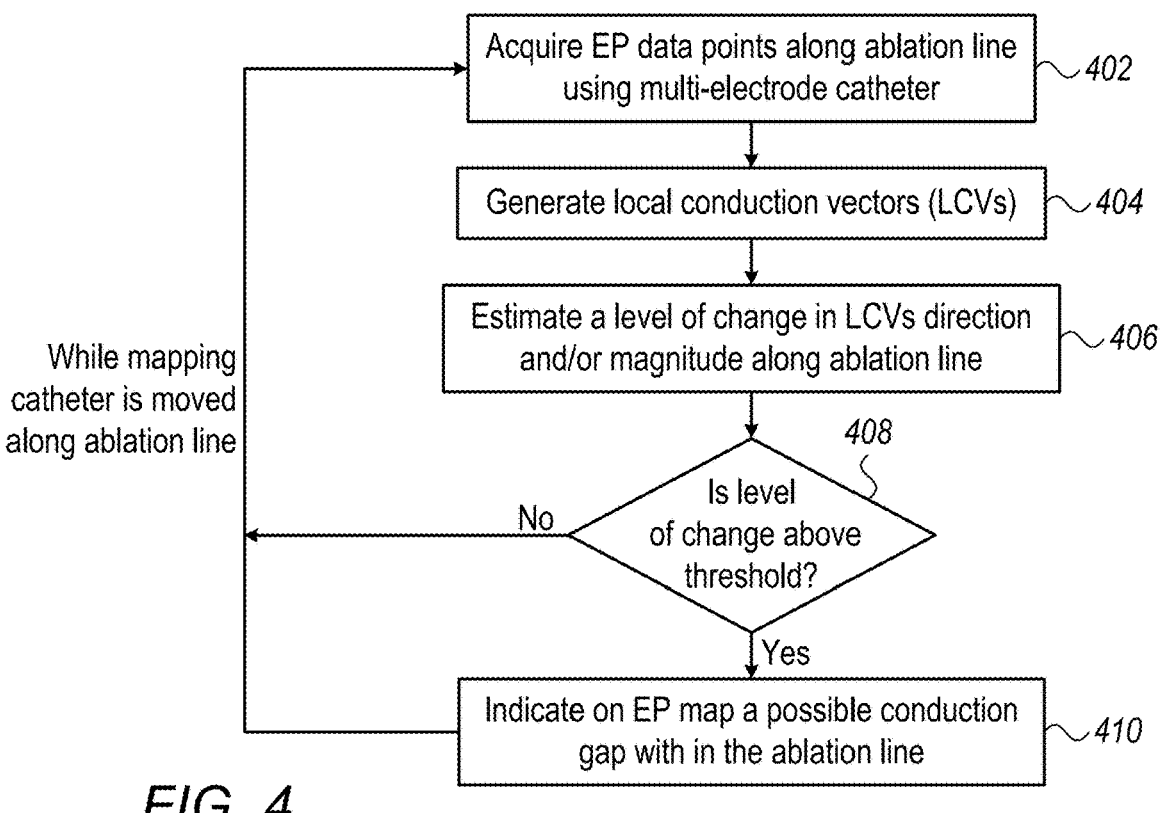

Acquire EP data points along ablation line using multi-electrode catheter ~402

Generate local conduction vectors (LCVs) ~404

Estimate a level of change in LCVs direction and/or magnitude along ablation line ~406

Is level of change above threshold? 408

No

Yes

Indicate on EP map a possible conduction gap with in the ablation line ~410

While mapping catheter is moved along ablation line

*FIG. 4*

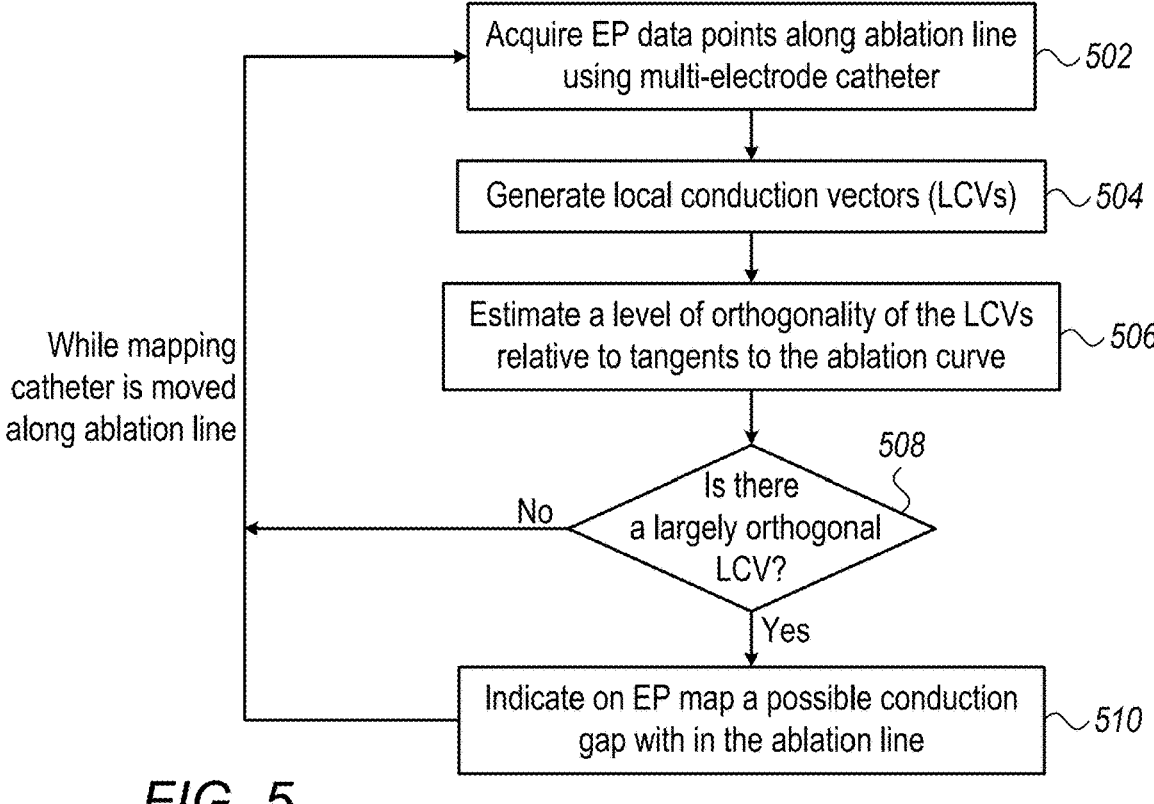

Acquire EP data points along ablation line using multi-electrode catheter ~502

Generate local conduction vectors (LCVs) ~504

Estimate a level of orthogonality of the LCVs relative to tangents to the ablation curve ~506

Is there a largely orthogonal LCV? 508

No

Yes

Indicate on EP map a possible conduction gap with in the ablation line ~510

While mapping catheter is moved along ablation line

*FIG. 5*

DETECTION OF ELECTROPHYSIOLOGICAL (EP) CONDUCTION GAPS IN ABLATION LINE

FIELD OF THE DISCLOSURE

This disclosure relates generally to acquisition and analysis of electrophysiological (EP) signals, and specifically to methods for identifying arrhythmogenic pathways using EP data acquired by an EP mapping catheter.

BACKGROUND OF THE DISCLOSURE

Identifying arrhythmogenic tissue pathways in heart tissue using a mapping catheter was previously proposed in the patent literature. For example, International Patent Application Publication WO 2020/227469 describes how pulmonary vein isolation (PVI) has become a first-line treatment for symptomatic drug refractory atrial fibrillation (AF). In the context of PVI procedures, linear ablation lesions are delivered in order to achieve PV isolation. Electrophysiological maps from data collected by high density grid catheters can be used to identify conduction gaps associated within circumferential pulmonary vein isolation lesions.

As another example, U.S. Patent Application Publication 2019/0125438 describes a method and system for gap detection in ablation lines. Microelectrodes are implemented at a distal tip of a catheter to provide localized gap detection along an ablation line. A pacing protocol is used to sequence through each of the microelectrode pairs for a tissue location. If living tissue is present, the pacing signal travels through the living tissue to pulse the heart. An operator will see a capture signal and know that there is a gap in the ablation line. Pacing and ablation are therefore performed at the same place without the need to switch between instruments and/or catheters.

U.S. Pat. No. 10,792,087 describes a method for assessing a gap in an ablation lesion, the method based on estimating a temporal relation between a stimulus and a sensed activation peaks and a spatial relation between the stimulus location and the sensing locations. This way, one of multiple electrodes of a sensing catheter proximal to a gap in the lesion is identified. A map of the body cavity is displayed with the identified electrode marked on the map.

In a paper incorporated herein by reference, the paper titled, "Propagation Vectors Facilitate Differentiation Between Conduction Block, Slow Conduction, and Wavefront Collision," in Circulation: Arrhythmia and Electrophysiology, Vol 14, pp. 741-550, August 2021, Yavin et al. describe how propagation vectors were created from unipolar waveforms of adjacent electrodes along and across catheter array splines that were acquired at single beats. To examine the utility of propagation vectors for detection conduction block during ablation, a Cavo tricuspid isthmus line was created during coronary sinus pacing with the array positioned lateral to the line. Real-time propagation vectors were found to enhance the ability of standard activation maps to differentiate between complex patterns of conduction, including determination of conduction block during ablation.

The present disclosure will be more fully understood from the following detailed description of the examples thereof, taken together with the drawings, in which:

BRIEF DESCRIPTION OF THE DRAWINGS

FIG. 4 is a flow chart that schematically illustrates a method to identify an ablation gap by discovering an abrupt change in LCVs, in accordance with an example of the present disclosure; and FIG. 5 is a flow chart that schematically illustrates a method to identify an ablation gap using absolute directions of LCVs, in accordance with an example of the present disclosure.

DETAILED DESCRIPTION OF EXAMPLES

Overview

Figure 1:
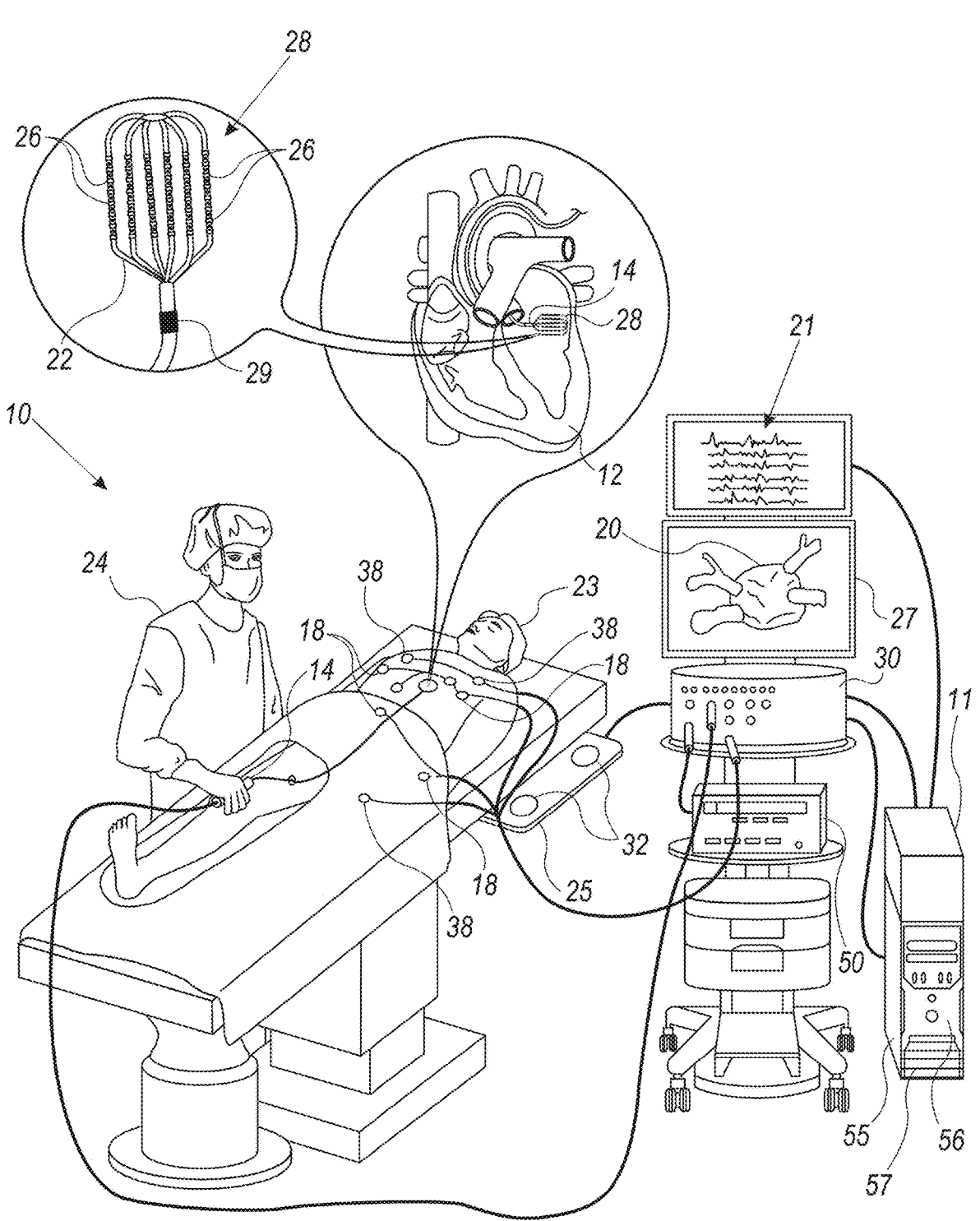
FIG. 1 is a schematic, pictorial illustration of a catheter-based electrophysiological (EP) mapping and ablation system, in accordance with an example of the present disclosure.

Catheter-based cardiac ablation may not always entirely terminate an arrhythmia as planned. For example, atrial fibrillation (AF) may persist despite performing pulmonary vein isolation (PVI) by ablating PV ostium tissue along a curve that covers an entire circumference of the PV ostium. Persistence of the arrhythmia may occur due to imperfect ablation, where one or more undesired gaps remain between otherwise contiguous ablation locations.

Typically, incomplete ablation requires a follow-up ablation. The additional ablation is best done during the same invasive procedure, i.e., immediately after checking for and identifying a gap following the first ablation. However, it is difficult to identify the locations of gaps along an ablation curve (the words "Ablation line" are also used, meaning the same path of ablation along a curve).

One possible way of obtaining an indication of the location of a gap is by mapping EP propagation in cardiac tissue. The propagation is analyzed from a plurality of EP data points acquired by a mapping catheter, each data point comprising an electrogram and a position over tissue where the electrogram was acquired. The data points are acquired from each electrode on the catheter, and the acquisition is performed automatically without user intervention.

For example, using these data points, a processor may compute local conduction vectors (LCV) that may by themselves alone indicate a gap. This indication, however, is often ambiguous and inaccurate. The analysis is difficult and the interpretation may be vague, due to natural variance in a distribution of the EP activation propagation vectors (e.g., LCVs).

To identify the exact location of a gap, therefore, the physician would need to (a) go over the target areas and at times (b) apply additional techniques such as pacing, which are time consuming. When using pacing, amplitudes at different timings and/or locations are compared. Searching for gaps based on amplitude lead to many false positives. In addition, pacing techniques alone also do not identify the exact location of the gaps.

One attempt to improve the analysis is described in U.S. patent application Ser. No. 17/481,616, titled, "Finding a Cardiac Line of Block Using Statistical Analysis of Activation Wave Velocity," filed Sep. 22, 2021. The application describes a method that includes receiving a set of data points including positions and respective velocities of an activation wave in a tissue region of a cardiac chamber. The set is partitioned into at least two velocity clusters, each velocity cluster characterized by a respective velocity of the activation wave. One or more border curves are estimated, between the at least two clusters. The one or more border curves are indicated to a user as possible lines of block of the activation wave.

Examples of the present disclosure that are described herein provide a user with a technique to readily detect any gaps in an ablation line in a manner that enables immediate re-ablation.

In one example, a processor identifies an ablation gap by detecting an abrupt change in the LCVs as the ablation line is scanned (e.g., traced by a physician) using the catheter. An abrupt change discovered in LCVs direction and/or magnitude indicates the existence of an ablation gap in therein or in close vicinity.

To estimate how abrupt is a change discovered in LCVs direction and/or magnitude, in some examples, a metric E(a,b) is defined between groups a and b of the LCVs. For example, let $V^a$ be the average vector of all vectors $v_i^a$ (i=1 . . . n) of group a of LCVs, and $V^b$ the average vector of all vectors $v_i^b$ (i=1 . . . n) of group b of LCVs. The calculation is for a muti-electrode catheter having n electrodes where at each LCV computation frame number k (for example at each heartbeat) a 3D vector $v_i^k$ is computed for each electrode i, i≤n. Then a distance metric between the vectors can be formulated as:

$$E(a,b)=(1-<V^a,V^b>)/2$$

The values of E(a,b) are in the range [0,1], where 0 indicates complete match and the value of 1 indicates complete opposite directions. A gap is indicated to a user if the metric value is larger than a predefined threshold c, E(a,b)>c, c>0. Other metrices are proposed below.

In other examples, a processor runs an algorithm that compares the direction of the LCV vectors to a local tangent of the ablation line. The algorithm runs in real time and may be used with or without pacing.

In some examples, to find ablation gaps, a processor performs the following steps after an ablation, and before starting the process of gap identification:

1. Computing an ablation line and displaying it on an EP map. The ablation line can be computed by, for example, interpolating over set of tags that mark the respective locations of ablation tissue sites (e.g., spots). To begin with, using a GUI, the line (e.g., path) is displayed, in one example, as a dashed pattern.
2. Guiding the physician (e.g., using the GUI) to navigate the catheter along the displayed ablation path. The covered portion of the path (that was analyzed), will became, in this example, a solid line.
3. Detecting one or more ablation gaps along the path.
4. Marking on an EP map any detected gaps on the path during the navigation (for example, in red colored line). This step may include overlaying the LCVs on the EP map.

In an example, gap detection step (3) is based on computing the aforementioned LCVs as the mapping catheter traces the ablation line. With high probability, if there are no gaps along the ablation line, the LCVs are expected to be more parallel (in average) to the ablation line direction. On the other hand, wherever there is a gap, the LCVs are expected to be oriented at a near perpendicular direction (i.e., near orthogonal to) with respect to the ablation lines at the location of the gap.

Checking the aforementioned level of orthogonality of LCVs can be performed in an automated method by comparing a direction tangent to the defined ablation path with a direction of an average of LCVs along a segment of the line being inspected. All the LCV related computations are performed in the background, and not necessarily displayed. The detected conduction gaps will be visually indicated by a special highlighting method on the map.

Finally, as a backup method that can be used with catheters that may not include acquisition capability sufficing to calculate LCVs, a processor may analyze acquired bipolar EP values along the ablation line. A local extremum of the changes in bipolar signal may be hint of a gap at that location.

System Description

FIG. 1 is a schematic, pictorial illustration of a catheter-based electrophysiology (EP) mapping and ablation system 10, in accordance with an example of the present disclosure.

System 10 includes multiple catheters, which are percutaneously inserted by physician 24 through the patient's vascular system into a chamber or vascular structure of a heart 12. Typically, a delivery sheath catheter is inserted into the left or right atrium near a desired location in heart 12. Thereafter, a plurality of catheters can be inserted into the delivery sheath catheter so as to arrive at the desired location. The plurality of catheters may include catheters dedicated for sensing Intracardiac Electrogram (IEGM) signals, catheters dedicated for ablating and/or catheters dedicated for both sensing and ablating. An example catheter 14 that is configured for sensing IEGM is illustrated herein. Physician 24 brings a distal tip 28 (also called hereinafter "distal-end assembly 28") of catheter 14 into contact with the heart wall for sensing a target site in heart 12. For ablation, physician 24 would similarly bring a distal end of an ablation catheter to a target site for ablating.

Catheter 14 is an exemplary catheter that includes one and preferably multiple electrodes 26 optionally distributed over a plurality of splines 22 at distal tip 28 and configured to sense the IEGM signals. Catheter 14 may additionally include a position sensor 29 embedded in or near distal tip 28 for tracking position and orientation of distal tip 28. Optionally and preferably, position sensor 29 is a magnetic based position sensor including three magnetic coils for sensing three-dimensional (3D) position and orientation.

Magnetic based position sensor 29 may be operated together with a location pad 25 including a plurality of magnetic coils 32 configured to generate magnetic fields in a predefined working volume. Real time position of distal tip 28 of catheter 14 may be tracked based on magnetic fields generated with location pad 25 and sensed by magnetic based position sensor 29. Details of the magnetic based position sensing technology are described in U.S. Pat. Nos. 5,391,199; 5,443,489; 5,558,091; 6,172,499; 6,239,724; 6,332,089; 6,484,118; 6,618,612; 6,690,963; 6,788,967; 6,892,091.

System 10 includes one or more electrode patches 38 positioned for skin contact on patient 23 to establish location reference for location pad 25 as well as impedance-based tracking of electrodes 26. For impedance-based tracking, electrical current is directed toward electrodes 26 and sensed at electrode skin patches 38 so that the location of each electrode can be triangulated via the electrode patches 38. Details of the impedance-based location tracking technology are described in U.S. Pat. Nos. 7,536,218; 7,756,576; 7,848, 787; 7,869,865; and 8,456,182.

A recorder 11 displays electrograms 21 captured with body surface ECG electrodes 18 and intracardiac electrograms (IEGM) captured with electrodes 26 of catheter 14. Recorder 11 may include pacing capability for pacing the heart rhythm and/or may be electrically connected to a standalone pacer.

System 10 may include an ablation energy generator 50 that is adapted to conduct ablative energy to one or more of electrodes at a distal tip of a catheter configured for ablating. Energy produced by ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

Patient interface unit (PIU) 30 is an interface configured to establish electrical communication between catheters, electrophysiological equipment, power supply and a workstation 55 for controlling operation of system 10. Electrophysiological equipment of system 10 may include for example, multiple catheters, location pad 25, body surface ECG electrodes 18, electrode patches 38, ablation energy generator 50, and recorder 11. Optionally and preferably, PIU 30 additionally includes processing capability for implementing real-time computations of location of the catheters and for performing ECG calculations.

Workstation 55 includes memory 57, processor 56 unit with memory or storage with appropriate operating software loaded therein, and user interface capability. Workstation 55 may provide multiple functions, optionally including (1) modeling the endocardial anatomy in three-dimensions (3D) and rendering the model or anatomical map 20 for display on a display device 27, (2) displaying on display device 27 activation sequences (or other data) compiled from recorded electrograms 21 in representative visual indicia or imagery superimposed on the rendered anatomical map 20, (3) displaying real-time location and orientation of multiple catheters within the heart chamber, and (5) displaying on display device 27 sites of interest such as places where ablation energy has been applied. One commercial product embodying elements of the system 10 is available as the CARTO™ 3 System, available from Biosense Webster, Inc., 31A Technology Drive, Irvine, CA 92618.

In some examples, processor 56, typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

This particular configuration of system 10 is shown by way of example, in order to illustrate certain problems that are addressed by examples of the present disclosure and to demonstrate the application of these examples in enhancing the performance of such a system. Examples of the present disclosure, however, are by no means limited to this specific sort of example system, and the principles described herein may similarly be applied to other sorts of medical systems. For example, other types of multi-electrode catheter may be used, such as the Octaray™ catheter or a basket catheter.

Identifying Ablation Gaps Along Ablation Path by Discovering Abrupt Change in LCVs To identify an ablation gap, a physician may perform EP mapping along an ablation line, by moving distal-end assembly 28 of mapping catheter 14, for example, from an earliest ablation location. As noted above, the entire path would initially be displayed dashed. The processor guides the physician, e.g., using a GUI, on the direction to move the mapping catheter along the path. The path portion that the mapping catheter covered is displayed continuous in FIG. 3.

Also seen is an ablation catheter 231 having an ablation electrode 232. This catheter was used in the first ablation that is checked for continuity. Catheter 231 will be used for a follow up ablation, to close any conduction gap found using the disclosed technique.

Figure 2B:
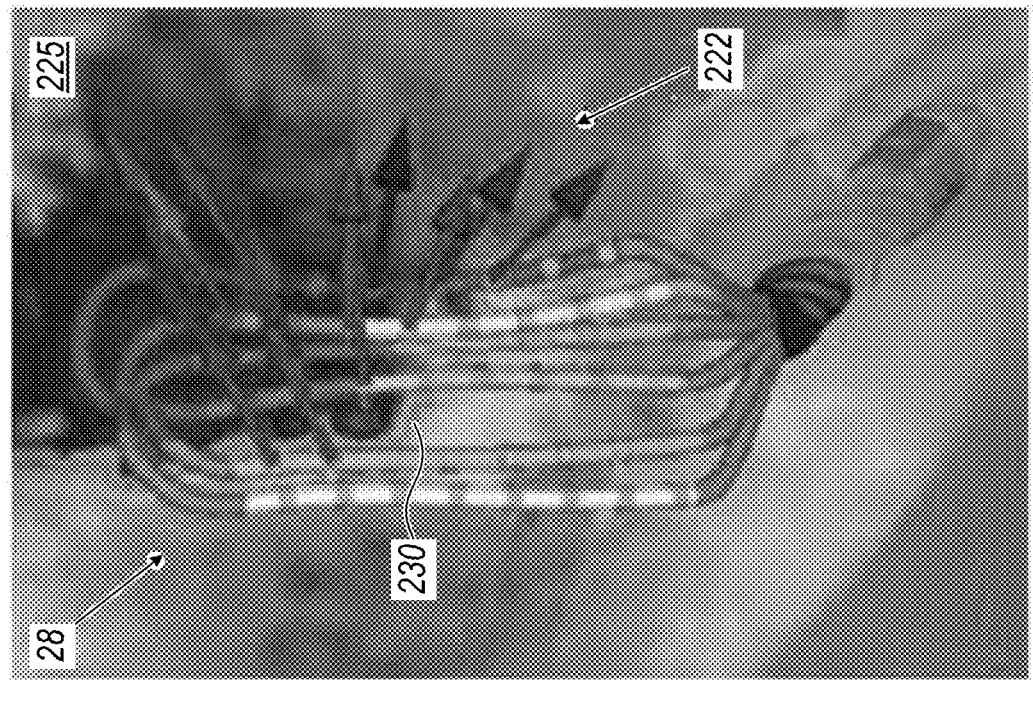
FIGS. 2A and 2B are renderings of an EP map of a cardiac chamber overlaid with respective sets of local conduction vectors (LCVs) showing abrupt change between sets that is indicative of an ablation gap, in accordance with an example of the present disclosure.
Figure 2A:
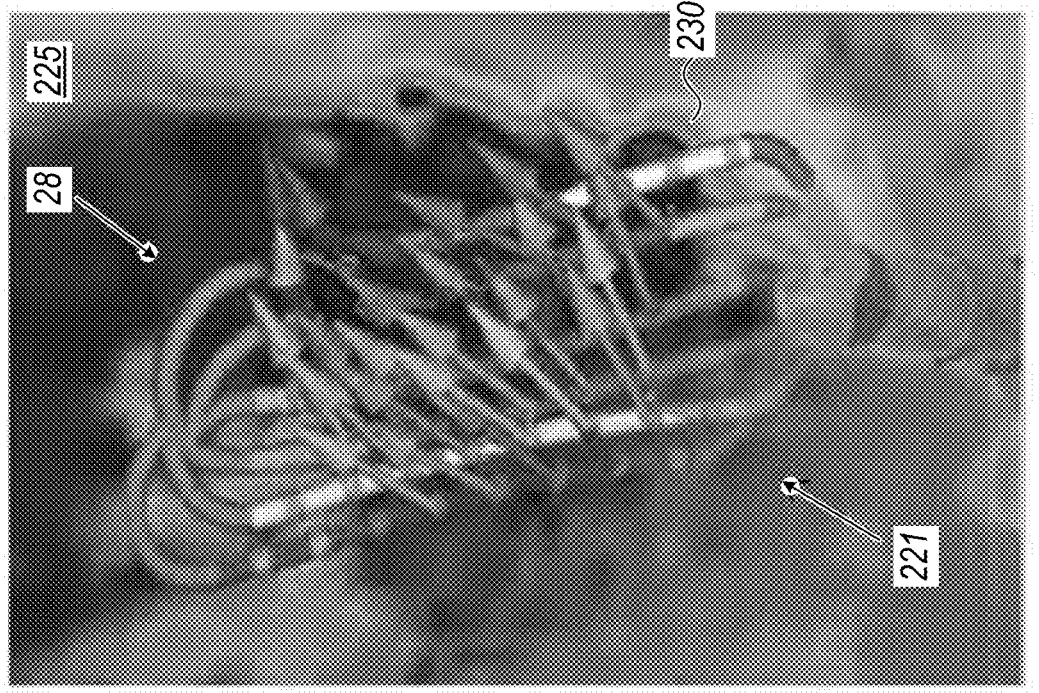

FIGS. 2A and 2B are renderings of an EP map 225 of a cardiac chamber overlaid with respective sets 221 and 222 of local conduction vectors (LCVs) showing abrupt change between sets that is indicative of an ablation gap, in accordance with an example of the present disclosure. The abrupt change in direction occurs at a tissue site along an ablation line 230.

To realize this, a system, such as system 10 includes an interface configured to receive multiple electrophysiological (EP) signals from tissue area along an ablation curve inside a cardiac chamber of a heart of patient. The processor of system 10 is configured to (i) indicate to a user the ablation curve along which to acquire the multiple EP signals, (ii) based on the multiple EP signals, generate local conduction vectors (LCVs) for the area, (iii) estimate a level of change between sets of LCVs along the ablation curve within the area, (iv) and based on the level of change, indicate a presence of a conduction gap in the ablation curve. The processor is configured to estimate the level of change by comparing the level of change to a predefined change threshold.

The processor is configured to estimate the level of change by generating for each set a representative LCV and estimate a level of change between the representative LCVs. The estimation of change may involve using one of the metrices described below:

A Metric for Measuring Change in LCVs

Having n electrodes where at each LCV computation frame number k (for example at each heartbeat) a 3D vector $$v_i^k$$

is computed for each electrode i, i≤n. Vectors $$v_i^k$$

are all normalized and have a length of 1.

Several metrics can be considered for Identifying overall vector changes between frames.

Having two frames a and b (with vectors $$v_i^a$$

and $$v_i^b$$

respectively). All vectors discussed herein are unit length vectors, and <x,y> stands for the inner product between vectors x and y.

Let $V^a$ be the average vector of all vectors $$v_i^a (i = 1 \ldots n),$$

and $V^b$ the average vector of all vectors $$v_i^b (i = 1 \ldots n)$$

Then one distance metric between the vectors can be formulated as:

$$E(a,b) = (1 - \langle V^a, V^b \rangle)/2$$

Another metric that can be applied is by using $L_2$ distance metric over the angle changes between the corresponding vectors over the frames, however this metric is slightly more expensive computationally.

$$E(a, b) = \frac{1}{2} \sqrt[2]{\sum_{i=1}^{n} w_i \left(1 - \langle v_i^a, v_i^b \rangle\right)^2}$$

where: $w_i$ is the weight of the change of the vector $v_i$. The weighting enables considering more information/parameters of interest to the formula, such as: voltage, position in the catheter grid. It is important to have positive normalized weights, such that:

$$\sum_{i=1}^{n} w_i = 1, w_i \geq 0$$

Other distance metrics other than $L_2$ can be used as well, such as $L_1$, $L_n$, $L_\infty$.

For stability purposes, the above computation can be done not necessarily between two consecutive frames, but rather between two averages of several frames. For example, each of the vectors of each three consecutive frames are averaged, and the comparison (the computation metric above is performed between two following averages (involving six frames)).

Figure 3B:
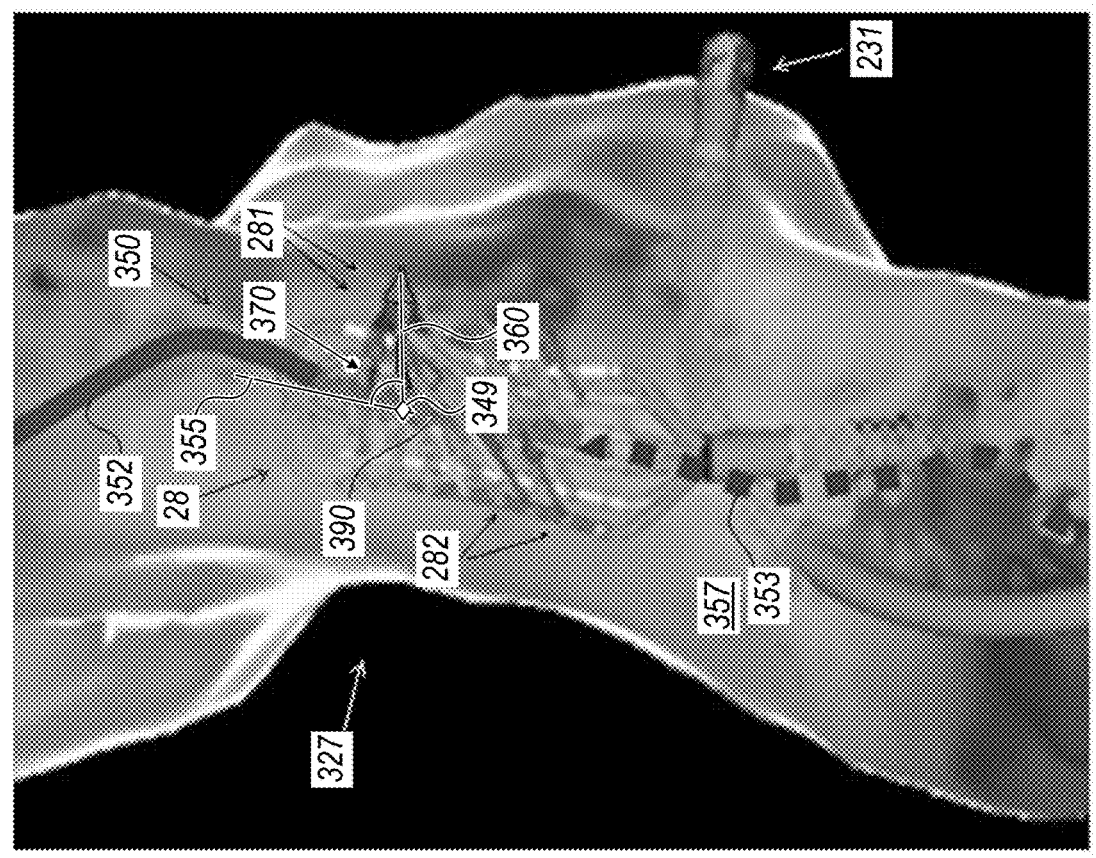
FIGS. 3A and 3B are renderings of EP maps of cardiac chambers, which respectively demonstrate, near antiparallel LCVs indicative of contiguous ablation, and near orthogonal LCVs indictive of a gap in ablation, in accordance with an example of the present disclosure.
Figure 3A:
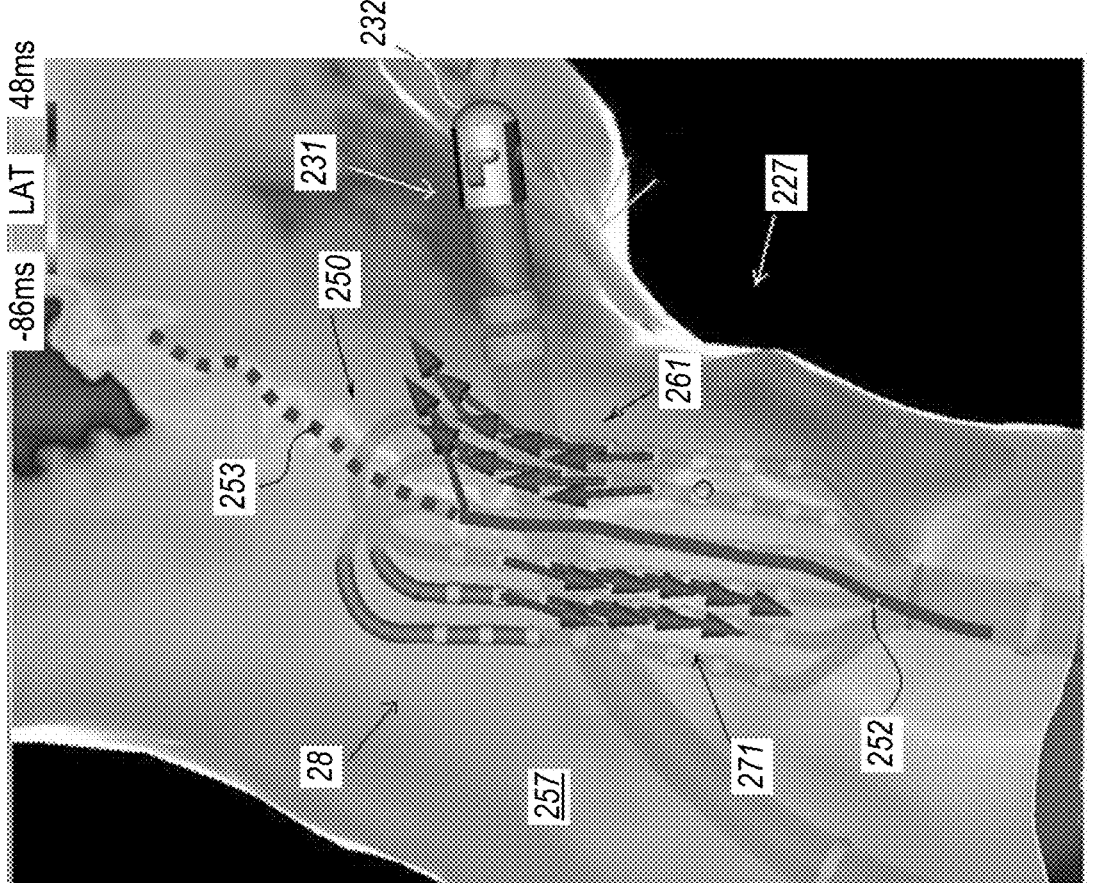

Identifying Ablation Gaps Along Ablation Path by Estimating Absolute Orientation of LCVs FIGS. 3A and 3B are renderings of EP maps 227 and 327 of a cardiac chamber 257 and 357, respectively, which demonstrate, in FIG. 3A, antiparallel LCVs (261, 271) indicative of contiguous ablation, and in FIG. 3B, near orthogonal LCVs (281, 282) indictive of a gap in ablation, in accordance with an example of the present disclosure.

In FIG. 3A, distal-end assembly 28 of catheter 14 of FIG. 1 is being advanced distally along an ablation line 250 that the processor drew. As seen, a portion 252 of line 250, which was already checked using the electrodes of distal-end assembly, is marked as a solid line, while remaining portion 253 is still displayed dashed. In the example shown in FIG. 3A, the LCVs of vector sets (261, 271) on either side of portion 252 of ablation line 250 are largely orientated antiparallel one with another. EP propagation vectors that are parallel or antiparallel on either side of the ablation line indicate with high probability that the ablation there is complete, e.g., without conduction gaps.

In FIG. 3B, distal-end assembly 28 of catheter 14 of FIG. 1 is being pulled proximally along an ablation line 350. As seen, a portion 352 of line 350, which was already checked using the electrodes of distal-end assembly, is marked as a solid line, while remaining portion 353 is still dashed. In the example shown in FIG. 3B, some vectors of vector sets (271, 281) on either side of portion 252 of ablation line 250 are largely orientated perpendicular to the ablation line therein. This is exemplified at a location 349 where an angle 370 between a tangent 355 therein and an LCV direction 360 is sufficiently close to 90 degrees to make location 349 part of a gap. Presence of EP propagation vectors that are largely perpendicular the ablation line indicate with high probability that the ablation there is incomplete, e.g., with one or more conduction gaps present therein.

The location of the conduction gap is displayed by having a portion 390 of ablation line 350 being highlighted by the processor. By way of example, the highlighting can be changing a color of line segment 390 (e.g., from black to red).

Methods of Identifying Ablation Gaps Along Ablation Path

FIG. 4 is a flow chart that schematically illustrates a method to identify an ablation gap by discovering an abrupt change in LCVs, in accordance with an example of the present disclosure. The algorithm, according to the presented example, carries out a process that begins with acquiring EP data points along an ablation line inside a cardiac chamber such as cardiac chamber 225 using system 10 and the flat catheter assembly 28 of FIG. 1, at EP data acquisition step 402. To this end, processor 56 displays the ablation line 230 overlayed on an EP map, as shown in FIG. 2, and guides the physician in real-time, using graphical tools such as described in conjunction with FIG. 3, where to move the mapping catheter in order to acquire relevant EP data points.

In EP data analysis step 404, processor 56 run a program to generate local conduction vectors (LCVs), such as seen in FIG. 2.#

At a next LCV analysis step 406, the processor estimates a metric E(a, b), such as one of aforementioned metrices, along ablation curve.

At orthogonality check 408, the processor compares the found level of orthogonality to a predefined threshold (e.g., to minimum predefined angle). The orthogonality is measured compared to the ablation line direction at the location of the catheter. In such case a metric is used to measure whether the vectors are in general orthogonal. The above metrics also can be used between the vectors (LCVs) as $V^a$ and the tangent vector (direction) of the curve as $V^b$.

In this case the algorithm may take into account to what extent a majority of the vectors to be orthogonal to the path direction as an alternative method for using the metrics. The check may be done per each LCV or per a local set of LCVs, in a statistical manner (e.g., by checking a moving average of orthogonality).

In case the level of orthogonality is found above threshold, processor 56 indicates a presence of a conduction gap in the ablation curve, at a gap indication step 410.

Either case, the process returns to step 402 as long as the mapping catheter is being moved along the ablation line.

FIG. 5 is a flow chart that schematically illustrates a method to identify an ablation gap using absolute directions of LCVs, in accordance with an example of the present disclosure. The algorithm, according to the presented example, carries out a process that begins with acquiring EP data points along an ablation line inside a cardiac chamber such as cardiac chamber 357 using system 10 and the flat catheter assembly 28 of FIG. 1, at EP data acquisition step 502. To this end, processor 56 displays the ablation line overlayed on an EP map, as shown in FIGS. 2 and 3, and guides the physician in real-time, using graphical tools such as described in conjunction with FIGS. 2 and 3, where to move the mapping catheter in order to acquire relevant EP data points.

In EP data analysis step 504, processor 56 run a program to generate local conduction vectors (LCVs), such as seen in FIGS. 2 and 3#

At a next LCV analysis step 506, the processor estimates a level of orthogonality of the LCVs relative to one or more tangents to the ablation curve.

At orthogonality check 508, the processor compares the found level of orthogonality to a predefined threshold (e.g., to minimum predefined angle). The check may be done per each LCV or per a local set of LCVs, in a statistical manner (e.g., by checking a moving average of orthogonality).

In case the level of orthogonality is found above threshold, processor 56 indicates a presence of a conduction gap in the ablation curve, at a gap indication step 510.

Either case, the process returns to step 502 as long as the mapping catheter is being moved along the ablation line.

The flow charts shown in FIGS. 4 and 5 are chosen purely for the sake of conceptual clarity. The present example may also comprise additional steps of the algorithm, such as pre-selecting input EGMs based on indications of the degree of physical contact of the electrodes with diagnosed tissue from a contact force sensor. This and other possible steps are omitted from the disclosure herein purposely in order to provide a more simplified flow chart.

EXAMPLES

Example 1

A system (10) includes an interface (30) and a processor (56). The interface is configured to receive multiple electrophysiological (EP) signals from a tissue area along an ablation curve (230, 250) inside a cardiac chamber (257, 357) of a heart (12) of a patient (23). The processor is configured to (i) generate local conduction vectors (LCVs) (221, 222) for the area based on the multiple EP signals, (ii) estimate a level of change between sets of LCVs along the ablation curve within the tissue area, and (iii) based on the level of change, identify a presence of a conduction gap (390) in the ablation curve.#

Example 2

The system (10) according to example 1, wherein the processor (56) is configured to identify the gap (390) by comparing by comparing the level of change to a predefined change threshold.

Example 3

The system (10) according to any of examples 1 and 2, wherein the processor (56) is configured to estimate the level of change by estimating one or both of (i) a change in direction and (ii) a change in magnitude, of LCVs (221, 222).

Example 4

The system (10) according to any of examples 1 through 3, wherein the processor (56) is configured to estimate the level of change by generating a representative LCV for each set (221, 222) and estimating a level of change between the representative LCVs.

Example 5

The system (10) according to any of examples 1 through 4, wherein the processor (56) is configured to indicate the ablation curve (230, 250) to a user by interpolating over a set of tags that mark the respective locations of ablation tissue sites and presenting a resulting interpolation curve.

Example 6

The system (10) according to any of examples 1 through 5, wherein the multiple electrophysiological (EP) signals are one of unipolar and bipolar electrograms acquired using a multi-electrode mapping catheter (14).

Example 7

The system (10) according to any of examples 1 through 6, wherein the ablation line (230, 250) is an ablation curve over a circumference of an ostium of a pulmonary vein (PV).

Example 8

A system (10) includes an interface (30) and a processor (56). The interface (30) is configured to receive multiple electrophysiological (EP) signals acquired in a tissue area along an ablation curve (230, 250) inside a cardiac chamber (257, 357) of a heart (12) of a patient (23). The processor (56) which is configured to (i) generate local conduction vectors (LCVs) (261, 271, 281, 282) for the tissue area based on the multiple EP signals, (ii) estimate a level of orthogonality of the LCVs relative to one or more tangents (355) to the ablation curve (230, 250) within the tissue area, and (iii) based on the level of orthogonality, identify a presence of a conduction gap (390) in the ablation curve.

Example 9

The system (10) according to example 8, wherein the processor (56) is configured to identify the gap (390) by comparing the level of orthogonality to a predefined threshold.

Example 10

The system (10) according to any of examples 8 and 9, wherein the processor (56) is configured to estimate the level of orthogonality by running a moving average of LCV level orthogonality for LCVs along the ablation line (230, 250).

Example 11

A method includes receiving multiple electrophysiological (EP) signals from a tissue area along an ablation curve (230, 250) inside a cardiac chamber (257, 357) of a heart (12) of a patient (23). Local conduction vectors (LCVs) (221, 222) are generated for the area based on the multiple EP signals. A level of change is estimated between sets of LCVs (221, 222) along the ablation curve within the tissue area. Based on the level of change, a presence of a conduction gap (390) is identified in the ablation curve (230, 250).

Example 12

A method includes receiving multiple electrophysiological (EP) signals acquired in a tissue area along an ablation curve (230, 250) inside a cardiac chamber (257, 357) of a heart (12) of a patient (23). Local conduction vectors (LCVs) (261, 271, 281, 282) are generated for the tissue area based on the multiple EP signals. A level of orthogonality is estimated, of the LCVs (261, 271, 281, 282) relative to one or more tangents (355) to the ablation curve (230, 250) within the tissue area. Based on the level of orthogonality, a presence of a conduction gap (390) is identified in the ablation curve.

Although the examples described herein mainly address cardiac diagnostic applications, the methods and systems described herein can also be used in other medical applications.

It will be appreciated that the examples described above are cited by way of example, and that the present disclosure is not limited to what has been particularly shown and described hereinabove. Rather, the scope of the present disclosure includes both combinations and subcombinations of the various features described hereinabove, as well as variations and modifications thereof which would occur to persons skilled in the art upon reading the foregoing description and which are not disclosed in the prior art.

The invention claimed is:

1. A system, comprising:
an interface configured to receive multiple electrophysiological (EP) signals from a tissue area along an ablation curve inside a cardiac chamber of a heart of a patient; and
a processor, which is configured to:
   generate local conduction vectors (LCVs) for the area based on the multiple EP signals;
   estimate a level of change between sets of LCVs along the ablation curve within the tissue area, wherein the processor estimates the level of change between the sets of LCVs based on a metric that comprises at least one of distance, angle, or length; and
   based on the level of change, identify a presence of a conduction gap in the ablation curve.

2. The system according to claim 1, wherein the processor is configured to identify the gap by comparing the level of change to a predefined change threshold.

3. The system according to claim 1, wherein the processor is configured to estimate the level of change by estimating one or both of (i) a change in direction and (ii) a change in magnitude, of LCVs.

4. The system according to claim 1, wherein the processor is configured to estimate the level of change by generating a representative LCV for each set and estimating a level of change between the representative LCVs.

5. The system according to claim 1, wherein the processor is configured to indicate the ablation curve to a user by interpolating over a set of tags that mark respective locations of ablation tissue sites and presenting a resulting interpolation curve.

6. The system according to claim 1, wherein the multiple electrophysiological (EP) signals are one of unipolar and bipolar electrograms acquired using a multi-electrode mapping catheter.

7. The system according to claim 1, wherein the ablation curve follows a circumference of an ostium of a pulmonary vein (PV).

8. A method, comprising:
receiving multiple electrophysiological (EP) signals from a tissue area along an ablation curve inside a cardiac chamber of a heart of a patient;
generating local conduction vectors (LCVs) for the area based on the multiple EP signals;
estimating a level of change between sets of LCVs along the ablation curve within the tissue area, wherein a processor estimates the level of change between the sets of LCVs based on a metric that comprises at least one of distance, angle, or length; and
based on the level of change, identifying a presence of a conduction gap in the ablation curve.

9. The method according to claim 8, wherein identifying the gap comprises comparing the level of change to a predefined change threshold.

10. The method according to claim 8, wherein estimating the level of change comprises estimating one or both of (i) a change in direction and (ii) a change in magnitude, of LCVs.

11. The method according to claim 8, wherein estimating the level of change comprises generating a representative LCV for each set and estimating a level of change between the representative LCVs.

12. The method according to claim 8, wherein indicating the ablation curve to a user comprises interpolating over a set of tags that mark respective locations of ablation tissue sites and presenting a resulting interpolation curve.

13. The method according to claim 8, wherein the multiple electrophysiological (EP) signals are one of unipolar and bipolar electrograms acquired using a multi-electrode mapping catheter.

14. The method according to claim 8, wherein the ablation curve follows a circumference of an ostium of a pulmonary vein (PV).

\*    \*    \*    \*    \*